United States Patent
Shanbrom (12)

(10) Patent No.: US 6,183,764 B1
(45) Date of Patent: Feb. 6, 2001

(54) MICROBICIDE TREATED POLYMERIC MATERIALS

(75) Inventor: Edward Shanbrom, Santa Ana, CA (US)

(73) Assignee: Shanbrom Technologies, Ojai, CA (US)

(*) Notice: Under 35 U.S.C. 154(b), the term of this patent shall be extended for 0 days.

(21) Appl. No.: 09/158,939

(22) Filed: Sep. 22, 1998

Related U.S. Application Data

(63) Continuation-in-part of application No. 08/929,415, filed on Sep. 15, 1997, now Pat. No. 5,811,471.

(51) Int. Cl.$^7$ .................................................. A01N 25/00
(52) U.S. Cl. ..................... 424/405; 424/484; 424/486; 521/94; 521/98; 521/128; 521/143; 521/145; 521/146; 521/149; 521/154
(58) Field of Search ............................. 521/94, 154, 182, 521/145, 128, 143, 146, 149; 424/405, 484, 486

(56) References Cited

U.S. PATENT DOCUMENTS 3,635,652 * 1/1972 Streck ..................................... 521/55
4,016,133 * 4/1977 Hyosu et al. .......................... 526/273
4,666,949 * 5/1987 Shimizu et al. ....................... 521/114

* cited by examiner

*Primary Examiner*—Morton Foelak
(74) *Attorney, Agent, or Firm*—Hogan & Hartson, L.L.P.

(57) ABSTRACT

A microbicidal organic polymer material for use in manufacturing of contact lenses, condoms, surgical sutures and gloves, medical examination devices and similar uses is provided by polymers to which is tightly adsorbed a disinfectant organic dye. Many polymers such as polyvinyl chloride and acrylic polymers show exceptional avidity for a number of microbicides, of acidic, basic, aromatic and/or hydrophobic character such as methylene blue and gentian violet. Consequently, devices constructed of these polymeric materials release no free dye to an aqueous solution. The material is generally a natural or synthetic polymer that releases no particles or fines into wounds or body orifices. Presence of adsorbed disinfectant organic dye allows the polymer to inhibit microbial growth in a number of different situations. Several common microbes are killed by being incubated in the present of an embodiment of the invention which contains a combination of methylene blue and gentian violet.

4 Claims, No Drawings

MICROBICIDE TREATED POLYMERIC MATERIALS

The instant application is a continuation-in-part of application Ser. No. 08/929,415, filed Sep. 15, 1997, now issued as U.S. Pat. No. 5,811,471.

BACKGROUND OF THE INVENTION

1. Field of the Invention

The present invention is related to the medical products and personal care products and especially to natural and synthetic polymers used to manufacture contact lenses, polymeric medical sutures, surgical gloves, and other similar medical items.

2. Description of Related Art

The importance of sterile techniques to modem medicine can hardly be overestimated. Almost every medical student is aware of infections introduced during surgery or during post surgical care and all users of contact lenses are familiar with the importance of clean contact lenses to the health of their eyes. A continuing problem with the use of polymeric materials has been the propensity for microorganisms to adhere to surfaces of these initially sterile polymeric materials which subsequently can lead to irritation and/or infection.

The principal uses of sterile grade polymers puts them in contact with various mucosal and other surfaces of the human and mammalian body. These surfaces are key in the body's early line of defense. When mucosal surfaces are abraded, penetrated incorrectly or exposed to conditions conducive to microbial growth, infection can occur more easily. In order to inhibit infection, the polymeric materials coming in contact with mucosal surfaces could be treated with some type of microbicide to inhibit microbial adhesion and subsequent infection. Unfortunately, it has proven difficult to produce an effective microbicide that does not readily wash out of the material, thereby greatly reducing its effectiveness and possibly causing irritation or damage to body tissues.

In most cases these products consisting of polymers are sterilized prior to packaging by gaseous treatment or irradiation, once in contact with air or mucosal surfaces they can act as an adherent surface for microbes. Various microbicides have been investigated but in most cases they are released from the polymer under aqueous conditions and they are more or less toxic. What is needed is a microbicide which remains adsorbed to the polymeric material under various physiological conditions where it can inhibit microbial growth without having negative effect on living tissue.

OBJECTS AND SUMMARY OF THE INVENTION

Therefore, it is an object of the present invention to provide adsorbent materials with anti-microbial properties for use in devices which ideally can remain in contact with mammalian mucosal surfaces for short to medium term duration without introducing or supporting microbial growth.

It is a further object of the current invention that the adsorbent not release microbicide which is toxic or which can cause possible irritation to surrounding tissues.

These and additional objects that will become apparent to one of ordinary skill in the art upon reading the following specification are provided through the use of polymers treated with gentian violet and/or the microbicidal components of the vaccinium species, blueberry, bilberry, cranberry, lingonberry and aroniaberry. These polymers demonstrate sufficient avidity to remove a number of microbicides from physiological solutions, including those mentioned above. Consequently, devices constructed of these materials, which have been treated with microbicide(s), release insignificant quantities of microbicide into aqueous solution. The material is generally a polymer that releases no particles or fines into body orifices or onto body surfaces. The presence of adsorbed microbicide(s) allows the polymer to inhibit microbial growth in a number of different situations. This makes the invention ideal for any uses where microbe-free adsorbent material is needed.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of treating the polymer with an adsorbed microbicide from a concentrated solution of gentian violet or other microbicidal/disinfectant dye in order to provide polymeric surfaces which resist microbial growth significantly more than their untreated equivalent.

By "microbicide" of "disinfectant" is meant any of a number of organic dyes, generally known as "vital dyes," including methylene blue and related thionine dyes (electronegative or acidic), acridine orange, acridine yellow and related acriflavine (acridine) dyes (electropositive or basic), quinacrine and its derivatives, brilliant green, gentian violet, crystal violet and related triphenyl methane dyes (electropositive), and bis naphthalene microbicides such as trypan blue and trypan. Methylene blue and gentian violet are especially preferred, but the invention is not limited to these organic dyes.

The cause of the microbicidal property of the dyes is not entirely known. Since many of the dyes have oxidation-reduction (redox) potentials in the range of many electron transport components of oxidative metabolism, it seems possible that these dyes may operate by "short circuiting" electron transport pathways. Generally, the dyes show differential activity towards Gram-negative versus Gram-positive bacteria with electronegative (acidic) dyes being more effective on Gram-negative bacteria and electropositive (basic) dyes being more effective on Gram-positive bacteria such as *Staphylococcus aureus*.

In the parent of the present application the inventor discovered that disinfectant dyes bind strongly to polyvinyl acetal (PVA) forming a germicidal or bacteria resistant material. In the course of those studies the present inventor discovered that a variety of plastic polymers such as polyvinyl chloride also binds the disinfectant dyes although, in some cases, not as effectively as PVA. Nevertheless, polymers treated with disinfectant dyes become highly resistant to bacterial growth—even causing a "zone of inhibition" when placed on a bacterial culture plate. The useable polymers include at least polyvinyl chloride, latex, polyurethanes, polyacrylates, polyester (polyethylene terephthlate) polymethacrylates, silicone rubber (and related silicon elastomers) polystyrene, polycarbonates and polysulfones. The polymers, polyvinylchloride and hydroxymethylmethacrylate, used to demonstrate the present invention are medical grades that are already widely used in commercial manufacturing of surgical tubing and contact lenses, respectively. The relevant properties of these polymers are their ability to preferentially adsorb various microbicides or disinfectant dyes. When treated with the appropriate dye the polymers become more or less distinctly colored by the dye. However, in many applications, a colored polymer is not a drawback; especially when the color is an indication that the polymer is capable of resisting bacterial growth.

The antimicrobial material of the present invention is produced by adsorbing an effective quantity of one or more microbicides to an appropriate polymeric material. An "appropriate" polymeric material means a polymer with sufficient avidity for a particular microbicide in order to inhibit microbial adherence and/or infection in a variety of physiological conditions. For example, an acrylic plastic is used in "hard" contact lenses. When these lenses are pretreated with gentian violet or methylene blue, they are much less likely to provide a surface for microbial adherence and/or growth. This makes them less likely to lead to microbial infection of the eye. This can prolong the total useful life of the lenses and/or their time of use between cleaning procedures. Properties required for a given application are well known to those of skill in the art. Polymers that can be readily dyed with disinfectant dyes are already used in a variety of personal and medical care products e.g. polymeric contact lenses, condoms. The same grade of polymers can be used for those applications with the current invention. "Effective quantity" means enough microbicide to inhibit microbial growth over the projected period of use.

Generally, it is sufficient to soak the polymeric material in an excess volume of an aqueous solution of an appropriate disinfectant dye followed by thorough washing in solutions mimicking physiological conditions of use to remove non-absorbed dye. In many cases the process can be accelerated by including an organic solvent such as ethanol and/or ethoxyethanol. Of course, solvents that do not damage or dissolve the polymer must be selected. This process can be readily automated by checking the wash water spectrophotometrically to ensure complete removal of non-absorbed microbicide dye. Initial experiments have applied the microbicide in aqueous solution. Many of the microbicides are more soluble in ethanol than in water, this solvent can be used in cases where the polymer itself is not soluble in ethanol. Many microbicides are also quite soluble in glycerin, propylene glycol or ethylene glycol monomethyl ether. Therefore, treatment solutions containing 50% or more of one of these solvent may be very useful depending on the polymer to be treated. Other appropriate solvents are known to those of ordinary skill or can be readily determined by examining available tables of dye solvents and comparing these to the known solvent resistance of the various polymers.

In one test a 2×2 inch squares (one quarter inch thick) of polyvinyl chloride were covered with a 4 mg/ml aqueous solution of gentian violet (C.I. Basic Violet 3), and non-absorbed dye washed away with distilled water after a 30 min binding period. The treated polymer was then exposed to a 2.0 ml of a suspension of either *Escherichia coli* or *Staphylococcus epidermidis*. After a 30 min incubation, the squares were rinsed with physiological saline and introduce into bacterial nutrient broth. After 24 hr incubation at 37° C. the tube were read spectrophotometrically. While the *E. coli* showed a reading of 0.5 absorbance units the reading in the *S. epidermidis* samples was only slightly above background. Controls run with non-treated polymer showed readings of 1.2 and 0.8 absorbance units, respectively. This demonstrates the known result that basic dyes are more effective on Gram positive (Staphylococcus) than on Gram negative (Escherichia) microbe. The significant point here is that while a goal of the present invention is to suppress microbial growth, this experiment also demonstrates actual microbial killing.

A more realistic test of the present invention treated the 2×2 test squares with a mixture of both a basic (gentian violet) and an acidic (methylene blue) dye. The squares were treated with an aqueous stock solution containing 4 mg/ml of each of the two dyes. After washing, the squares were treated with 1.0 ml of microbial growth medium containing either 100 cells of *E. coli* or *S. epidermidis*. The squares were incubated for 24 hr at 37° C. and then read. As would be expected from the earlier experiment, all of the *S. epidermidis* cells were killed and no colonies grew up. Significantly, there were no colonies from the *E. coli* treatments either. Control material without the dyes showed abundant microbial growth. Significantly the dye mixture killed both Gram positive and Gram negative microbe. The experiment was repeated with *Yersinia enterocolitica* (Gram negative), *Serratia marcesceus* (Gram negative) and *Staphylococcus aureus* (Gram positive), and again there were no viable microbes following the treatment. Thus, a mixture of basic and acidic dyes adsorbed to polyvinyl chloride prevents the growth of a wide variety of common microbes. Repeating this experiment using blood or plasma as the microbial growth medium gave similar results indicating that an important goal of this invention, i.e., microbicidal activity in the presence of protein solutions, has been met. These experiments show that this material is ideal for medical or surgical grade materials, or polymeric contact lenses. The experiments were repeated using acrylic plastics and urethane plastics. The subject plastics were soaked in the dye solution for a sufficient period to become lightly colored. The bacterial results were substantially the same as with poly vinyl chloride. From this it would appear that the exact polymer used is not critical as long as it is capable of binding a visible amount of dye. Thus, the treatment period should be adjusted, depending on the polymer, to yield visible color.

Both methylene blue and crystal violet have a long history of topical use. They are generally non-irritating, and preliminary experiments indicate that dye treated polymer is also non-irritating. The unusual effectiveness of the present material is probably due to the adsorption of the dye to the polymer which prevents it from washing away and becoming to dilute to be effective. The adsorbed microbicide presents a very high local concentration that effectively eliminates microbes. Presumably, the microbicide either inhibits adherence or transfers from the polymer to the microbial cells in contact with the treated polymer thereby killing them. It is fairly easy to test materials for suitability in the present invention. Effective materials will become readily colored by when treated with the microbicides. Furthermore, extensive washing will be unable to remove the tightly adsorbed microbicide.

The current invention has been described as including the step of treating the formed polymer with a microbicide solution. This is currently the preferred method of making the treated polymer of the present invention although it is possible that the microbicide could be introduced during manufacture of the polymer, thereby simplifying the entire process.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

I claim:

1. An antimicrobial organic polymeric material for medical and personal use comprising:

an organic polymer selected from the group consisting of polyvinyl chloride, latex, polyurethane, polyacrylate, polyester, polyethylene terephthalate, polymethacrylate, silicone rubber, silicon elastomers, polystyrene, polycarbonate and polysulfones;

a mixture of water-soluble methylene blue and gentian violet dyes absorbed onto the organic polymer, wherein an aliquot of living bacterial cells in liquid nutrient medium placed on the antimicrobial organic polymeric material shows no growth of the living bacterial cells following incubation.

2. A glove made from the antimicrobial organic polymer of claim 1.

3. A contact lens made from the antimicrobial organic polymer of claim 1.

4. A condom made from the antimicrobial organic polymer of claim 1.

* * * * *

(12) EX PARTE REEXAMINATION CERTIFICATE (10678th)
United States Patent
Shanbrom

(10) Number: US 6,183,764 C1
(45) Certificate Issued: Aug. 12, 2015

(54) MICROBICIDE TREATED POLYMERIC MATERIALS

(75) Inventor: Edward Shanbrom, Santa Ana, CA (US)

(73) Assignee: SHANBROM TECHNOLOGIES LLC, Ojai, CA (US)

Reexamination Request:
No. 90/013,317, Aug. 12, 2014

Reexamination Certificate for:
Patent No.: 6,183,764
Issued: Feb. 6, 2001
Appl. No.: 09/158,939
Filed: Sep. 22, 1998

Related U.S. Application Data

(63) Continuation-in-part of application No. 08/929,415, filed on Sep. 15, 1997, now Pat. No. 5,811,471.

(51) Int. Cl.
*A61F 13/36* (2006.01)
*A61L 15/26* (2006.01)
*A61L 15/46* (2006.01)
*A61L 15/16* (2006.01)
*C08L 59/00* (2006.01)

(52) U.S. Cl.
CPC ................. *A61F 13/36* (2013.01); *A61L 15/26* (2013.01); *A61L 15/46* (2013.01); *C08L 59/00* (2013.01); *A61L 2300/404* (2013.01); *A61L 2300/412* (2013.01)

(58) Field of Classification Search
None
See application file for complete search history.

(56) References Cited

To view the complete listing of prior art documents cited during the proceeding for Reexamination Control Number 90/013,317, please refer to the USPTO's public Patent Application Information Retrieval (PAIR) system under the Display References tab.

*Primary Examiner* — Evelyn Huang

(57) ABSTRACT

A microbicidal organic polymer material for use in manufacturing of contact lenses, condoms, surgical sutures and gloves, medical examination devices and similar uses is provided by polymers to which is tightly adsorbed a disinfectant organic dye. Many polymers such as polyvinyl chloride and acrylic polymers show exceptional avidity for a number of microbicides, of acidic, basic, aromatic and/or hydrophobic character such as methylene blue and gentian violet. Consequently, devices constructed of these polymeric materials release no free dye to an aqueous solution. The material is generally a natural or synthetic polymer that releases no particles or fines into wounds or body orifices. Presence of adsorbed disinfectant organic dye allows the polymer to inhibit microbial growth in a number of different situations. Several common microbes are killed by being incubated in the present of an embodiment of the invention which contains a combination of methylene blue and gentian violet.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2-4 are cancelled.

Claim 1 is determined to be patentable as amended.

1. An antimicrobial organic polymeric material for medical and personal use comprising:

an organic polymer selected from the group consisting of polyvinyl chloride, latex, polyurethane, polyacrylate, polyester, polyethylene terephthalate, polymethacrylate, silicone rubber, silicon elastomers, polystyrene, polycarbonate and polysulfones;

[a mixture] *an antimicrobial amount of a microbicide consisting* of water-soluble methylene blue *dye absorbed onto the organic polymer;* and

*an antimicrobial amount of a microbicide consisting of water-soluble* gentian violet [dyes] *dye* absorbed onto the organic polymer, wherein [an aliquot] *aliquots* of living *Gram negative and Gram positive* bacterial cells in liquid nutrient medium placed on the antimicrobial organic polymeric material [shows] *show* no growth of the living bacterial cells following incubation.

* * * * *